United States Patent [19]

Hirschfeld

[11] Patent Number: 5,242,442
[45] Date of Patent: Sep. 7, 1993

[54] SMOKE ASPIRATING ELECTROSURGICAL DEVICE

[76] Inventor: Jack J. Hirschfeld, 244 Walton Heath Dr., Atlantis, Fla. 33462

[21] Appl. No.: 762,847

[22] Filed: Sep. 18, 1991

[51] Int. Cl.$^5$ .............................................. A61B 17/39
[52] U.S. Cl. ...................................... 606/42; 606/45; 606/49; 604/35
[58] Field of Search ................ 606/42, 45, 49; 604/35

[56] References Cited

U.S. PATENT DOCUMENTS

| | | |
|---|---|---|
| 2,275,167 | 4/1939 | Bierman . |
| 2,888,928 | 4/1957 | Seiger . |
| 3,035,580 | 12/1960 | Guiorguiev . |
| 3,906,955 | 9/1975 | Roberts . |
| 3,974,833 | 8/1976 | Durden, III ......................... 606/49 |
| 4,562,838 | 1/1986 | Walker . |
| 4,683,884 | 8/1987 | Hatfield et al. ....................... 606/49 |
| 4,719,914 | 1/1988 | Johnson ........................... 604/35 X |
| 4,919,129 | 4/1990 | Weber, Jr. et al. ............... 604/35 X |
| 5,071,418 | 12/1991 | Rosenbaum ......................... 606/42 |
| 5,085,657 | 2/1992 | Simhon ............................... 606/42 |

OTHER PUBLICATIONS

Johnson et al., "Smokeless Electrocautery Tonsillectomy," *ENTechnology*, Aug. 1990.
Young et al., "A Simple Method of Evacuating Smoke From Wounds," *Plastic and Reconstructive Surgery*, Nov. 1989, p. 855.
Thorne, "The Useful Smoke Sucker," *Plastic and Reconstructive Surgery*, Mar. 1986.

*Primary Examiner*—Lee S. Cohen
*Attorney, Agent, or Firm*—Quarles & Brady

[57] ABSTRACT

A smoke aspirating electrosurgical device includes an electrically conductive blade attached to an axial end of a device handle. The handle is constructed to form an interior channel extending from the blade end of the handle to the opposite end for aspiration of smoke produced by electrosurgical incisions with the blade. The interior channel can be connected to a vacuum source through a tube extending from the channel.

6 Claims, 16 Drawing Sheets

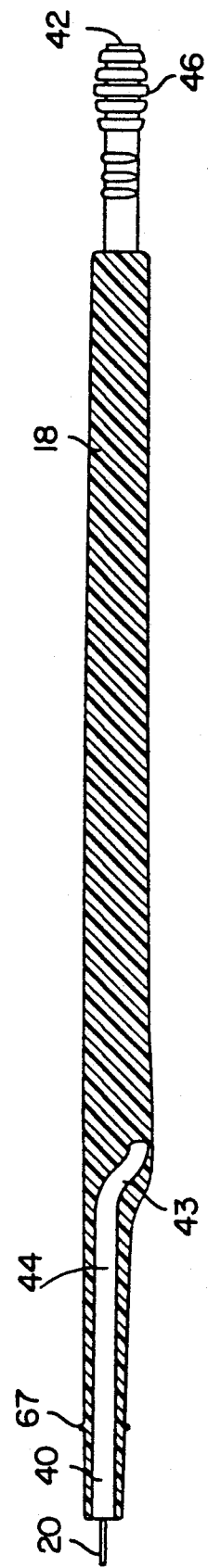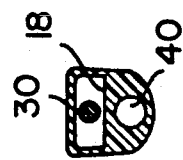
Figure 3a
Figure 3b

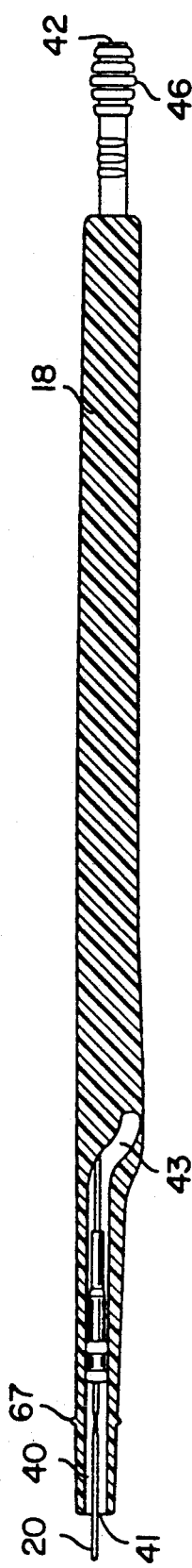
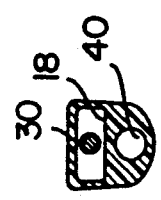
Figure 11a
Figure 11b

SMOKE ASPIRATING ELECTROSURGICAL DEVICE

BACKGROUND OF THE INVENTION

1. Field of the Invention

The present invention relates generally to electrosurgical devices for incising and cauterizing soft tissue and other anatomical structures. The present invention relates more particularly to electrosurgical devices which aspirate smoke produced by incision and cauterization.

2. Discussion of the Prior Art

Electrosurgical devices have been developed to substitute "cold" scalpels for incising soft tissue and other anatomical structures during surgical procedures. A typical electrosurgical device provides a blade or needle which represents one electrode in a circuit completed by a grounding electrode attached to an extremity of the patient. Electric power is applied to the electrode blade by appropriate means. Upon application of the electrically charged blade to the anatomical surface, a voltage gradient is created, thereby inducing current flow and related heat generation at the point of contact. A sufficiently large voltage gradient generates sufficient heat to incise or cut the tissue. Electrosurgical devices represent an improvement in incising instruments because the heat generated by an electrosurgical device can also cauterize the anatomical structure after incision to reduce or stop the associated bleeding.

Some electrosurgical devices have control circuitry for selectively generating a relatively high voltage for incision and relatively low voltage for cauterization only. Selection between the two levels can be made by manipulation of switch controls, such as buttons on a handle of the electrosurgical device.

Although electrosurgical devices provide many advantages, a significant drawback of their use is the smoke produced during incising and cauterization. Incision and cauterization using an electrosurgical device can generate substantial amounts of smoke. The smoke can obscure or impair the vision of the operating surgeon. Additionally, the smoke can be an irritant to the surgeon's eyes, thereby interfering with the progress of surgical procedures.

Smoke generation can be particularly troublesome in closed spaces, especially during intrathoracic, flap development and oropharyngeal procedures. In such operations, an extended blade is sometimes used to incise surfaces several inches inside a closed space cavity. The smoke generated at the point of incision can accumulate in the cavity. This accumulated smoke can severely obscure the surgeon's view of the operative site.

The smoke can also perpetuate the smell of burning flesh. This smell can be distracting to the operating surgeons, attending nurses and technicians as well as the patient, if conscious during the operating procedure.

Of particular significance and concern, it has been discovered that the smoke produced by electrosurgical incisions and cauterizations can contain and transport viable virile DNA. The viruses transmitted by the smoke present a significant health hazard to the operating surgeon and others present in the operating room.

Systems have been developed for aspirating smoke produced by electrosurgical procedures. In a typical technique, the smoke is aspirated by a conventional hospital suction tube held near the site of the electrosurgical procedure by a medical technician. This method inefficiently occupies the attention of a technician. The placement of the often bulky suction tube in the operative field can also obstruct the operating surgeon's view.

Other systems have been developed to overcome these disadvantages. In *Plastic and Reconstructive Surgery*, (Volume 85, No. 5, November, 1989, Page 855), Young et al. disclose smoke aspirating apparatus constructed piecemeal from various medical supplies available in an operating room. The apparatus includes a conventional catheter attached to the side of an electrocautery pencil so that the catheter inlet is positioned near the "cutting" end of the electrocautery blade. The catheter is secured to the electrocautery pencil by adhesive tape and is connected at its outlet end to standard hospital suction tubing.

The on-site construction of this apparatus prior to operation is inconvenient and can expose the assembler to puncture or cuts from the electrocautery needle or blade. Such wounds present a substantial health hazard during the subsequent operation.

Additionally, the adhesive tape used to secure the catheter to the electrocautery pencil can become saturated with blood and other fluids during the operating procedure and thereby unravel or disintegrate. Consequently, the catheter can become separated from the electrocautery pencil during the surgery. In addition to being inconvenient, the separating catheter can possibly injure the patient.

In closed space procedures in which the catheter is taped to an extended blade, the separation of tape inside the cavity presents a significant danger. Pieces of tape or adhesive can separate and become lost in the cavity. If these foreign bodies are not discovered and removed, post-operative infections can occur.

The taping of the catheter to the blade also interferes with the blade changing that is sometimes required during surgery. Further, the taped catheter can prevent cleaning of char which collects on the blade during surgery.

In *ENTechnology*, (August, 1990, Page 562), Johnson et al. have also disclosed apparatus for aspirating smoke during electrosurgical procedures. The apparatus is constructed by threading a needle tip of an electrosurgical pencil blade into the suction end of a catheter so that a few millimeters of the needle remain exposed to perform incision. The shrouding of the needle with the catheter provides insulation of the needle against inadvertent burning of tissue adjacent to the desired site.

In this construction, the catheter is again attached to the electrosurgical pencil by adhesive tape. Although the threading of the electrosurgical needle tip through the catheter end reduces the likelihood of separation at the tip, separation along the length of the electrosurgical device can nevertheless occur if the adhesive tape unravels or disintegrates.

The insertion of the electrosurgical needle tip through the suction end of the catheter increases the risk of puncture or cut to the assembling surgeon during construction. Such wounds can present a health risk during surgical procedures. Also, the shrouding catheter can interfere with blade changing during surgery, further increasing the risk of a puncture or cut.

SUMMARY OF THE INVENTION

It is an object of the invention to provide an electrosurgical device which will facilitate electrosurgical procedures.

It is another object of the invention to provide an electrosurgical device which will reduce the exposure to smoke and contaminates which interfere with electrosurgical procedures and present a health risk to surgeons and others.

It is still another object of the invention to provide an electrosurgical device which will effectively remove smoke during closed space electrosurgical procedures.

It is a still further object of the invention to provide an electrosurgical device with smoke aspirating structure which will allow easy blade changing and char cleaning.

These and further objects of the invention are achieved by an electrosurgical device having a blade handle that houses aspirating means for drawing smoke produced during incision or cauterization by the electrosurgical blade through the handle for subsequent evacuation. The handle walls can define an interior channel extending from a channel inlet adjacent the blade to a channel outlet formed at the opposite, rear end of the handle. The interior channel can be defined by the wall structure of the handle to form an integral passage along the length of the handle so that the handle can be manufactured by injection molding to provide an inexpensive, disposable device.

The aspirating means of the handle can be connected to a vacuum source in the operating room in a variety of ways. For example, the channel can enclose a lightweight tube that extends out of the channel outlet for coupling with a larger, standard hospital suction tube or directly with a vacuum port located on a wall or table in the operating room. Alternatively, the outlet end of the handle can provide an integrally formed adapter for connections directly to a standard hospital suction tube.

The internal channel can be formed within the handle so that the channel inlet surrounds the cutting portion of the blade. The channel can extend along the interior aspect of the handle to the channel outlet. In a preferred embodiment, the suction inlet is disposed above the cutting portion of the blade along the top of the electrosurgical device, whereby smoke rising from the incised or cauterized anatomical surface is more readily drawn into the suction inlet. The channel inlet can terminate close to the end of the blade and angle downwardly to increase the effectiveness of the smoke suction. The channel can transition from above the blade to a lower extension along the bottom of the handle to minimize the lateral thickness of the handle.

Although the aspirating means for conducting the smoke through the device handle can utilize an integral channel alone, the aspirating means can also include a flexible tube extending through the internal channel and out of the handle for connection to a conventional hospital suction tube or directly to a vacuum source in the operating room. Use of the tube can reduce the likelihood of electrical shorting of the device circuitry by fluids which may inadvertently be drawn into the handle. Further, the interior of the handle can be formed to provide an internal wall separating the smoke channel from the electric control circuitry of the device.

When it is necessary to make incisions in remote, closed space cavities, such as during thoracotomies, a blade having an extended shaft is typically used so that the cutting end of the blade can readily access a more remotely located, desired incision point in the chest cavity. The portion of the blade extending from the handle can be three or more inches in length. During these closed space incisions, evacuation of the smoke is most critical. The electrosurgical device of the invention can provide a suction extension removably connected to the handle adjacent the channel inlet and extending axially from the handle to provide a suction inlet proximate the cutting portion of an extended blade. The extension can be securely connected to the channel inlet of the handle and made of a rigid thermoplastic material so that no lateral support, such as by adhesive tape, is required.

BRIEF DESCRIPTION OF THE DRAWINGS

A fuller understanding of the present invention can be gained from a reading of the following detailed description in association with the accompanying drawings, in which:

FIG. 3a is a top sectional view of the first embodiment;

FIG. 3b is an axial sectional view along line 3b—3b in FIG. 1;

FIG. 11a is a top sectional view of the third embodiment;

FIG. 11b is an axial sectional view along line 11b—11b in FIG. 9;

DETAILED DESCRIPTION OF THE PREFERRED EMBODIMENTS

Figure 1:
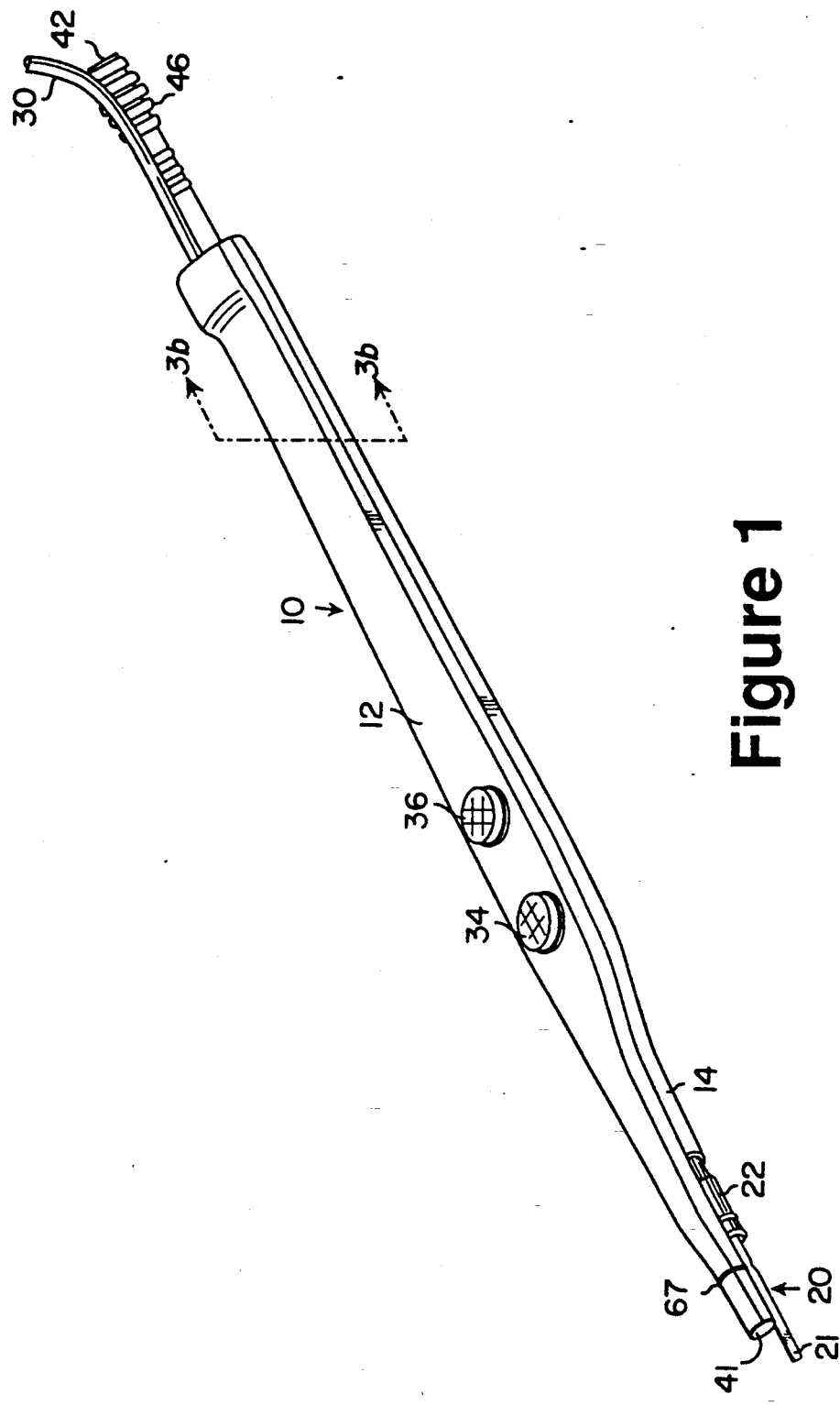
FIG. 1 shows a perspective view of a first embodiment of an electrosurgical device, wherein a channel inlet of the handle is disposed above the electrosurgical blade.

The present invention relates to electrosurgical devices for incising and cauterizing anatomical structures, such as soft tissue, mucosa, muscle and fat. The invention is more particularly related to electrosurgical devices and methods for aspirating smoke produced by the incision and cauterization of these anatomical structures.

Generally, the invention provides an electrosurgical device in which means for aspirating smoke produced by incision or cauterization with an electrosurgical blade is integrated into the handle for the electrosurgical blade. This aspirating means is preferably an interior channel integrally formed by the handle of the electrosurgical device for communicating smoke from the point of generation to a rear portion of the handle for subsequent evacuation.

Referring to the drawings, and particularly to FIGS. 1-4, which show a first embodiment of the invention, the electrosurgical device of the invention includes a handle 10 for holding and manipulating an electrosurgical blade 20. The handle 10 can be constructed in different shapes and sizes according to the desired specifications, but is preferably constructed as a slender, elongated body to be held comfortably by a surgeon in the manner of a writing instrument. The handle 10 can be injection molded using thermoplastic material to provide a lightweight, inexpensive, disposable device.

The blade 20 can be permanently attached to a forward end 14 of the handle 10, but is preferably removably mounted at the forward end 14 of the handle 10 to permit interchanging of blades of different lengths and blade configurations. The blade 20 is electrically conductive and generally made of metal.

Figure 2:
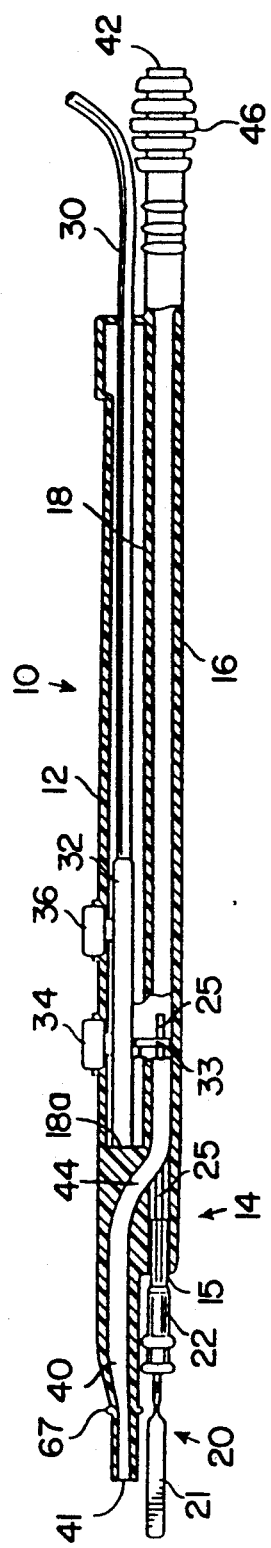
FIG. 2 is a side sectional view of the first embodiment.

Referring to FIG. 2, the blade 20 is supplied with electric power from a power source through electric connecting means, such as a wire 30, which extends through the interior of handle 10 for connection to switch circuitry 32 or directly to the blade 20. The electric wire 30 can provide electric power from a power source to the switch circuitry 32 in a variety of ways known in the art. The switch circuitry 32 for controlling the application of electric power to blade 20 can be provided in the interior of handle 10. This switch circuitry 32 can be actuated by switch control members, such as manually depressible buttons 34 and 36.

The electrosurgical device can have a single switch control member to control application of a single voltage level to the blade 20. However, the device preferably provides two control members, such as the buttons 34 and 36, to selectively control application of an incising voltage level and a lower, cauterizing voltage level to the blade 20. The components of the switch circuitry 32 which provide this stepped voltage to the blade 20 are known in the art.

The handle 10 preferably houses the switch circuitry 32 in an upper chamber defined by a top wall 12 of the handle 10 and a separating wall 18 extending axially in the interior of the handle 10. The separating wall 18 can include an upwardly extending end wall 18a for connection to the top wall 12. Upon depression of one of the switch control members 34, 36, the switch circuitry 32 connects electric power to a mounting shaft 25 of the blade 20 through a blade contact 33. In FIG. 2, the wall 18 and a tube 44 have been partially broken away to show the junction of the contact 33 and the blade shaft 25. The blade contact 33 can extend downwardly from the switch circuitry 32 through the separating wall 18 to slidingly receive the mounting shaft 25.

The cutting member 21 of the blade 20 can be constructed in a variety of shapes. The cutting member 21 can be formed to provide a flat, elongated, dull surface which incises anatomical structures by generation of heat rather than by a sharpened cutting surface. Alternatively, the cutting member 21 can be configured as an elongated needle. As blades with different lengths, configurations, and cutting members 21 can be necessary during an operation, various blades 20 can be interchanged with the handle 10 as required.

The blade 20 can be removably mounted in handle 10 through a mounting aperture 15 formed at the forward end 14 of the handle 10. A mounting sleeve 22 can be fixed to the mounting shaft 25 to provide a gripping surface for slidingly inserting and removing the blade 20 through the mounting aperture 15.

The electrosurgical device of the invention includes aspirating means integrally formed in the interior of the handle 10 for allowing the passage of smoke which is produced during incision or cauterization through the handle 10 for subsequent evacuation. The aspirating means can include an interior channel 40 formed in the handle 10. The channel 40 preferably extends from a channel inlet 41 formed on the blade end of the handle 10 to a channel outlet 42 formed on the opposite, rearward end of the handle 10. The channel 40 can be defined by the outer walls of the handle 10 and the separating wall 18 extending along the interior of the handle 10 to separate the smoke passage from the chamber enclosing the switch circuitry 32. Thus, an integrally formed smoke conduit is provided for the transfer of smoke through the handle 10.

The handle 10 can be constructed of a rigid material, such as a rigid thermoplastic. The integrally formed channel 40 is thereby rigidly positioned relative to the blade 20 and is not susceptible to motion during use. Thus, the positioning of the channel inlet 41 is fixed to optimize the effectiveness of the suction and is not upset during use.

The inlet 41 of the channel 40 is preferably configured to capture smoke rising from the blade 20. The top surface 12 of the handle 10 is oriented generally upwardly during use so that the switch controls 34 and 36 can be easily manipulated by the index finger of the surgeon. In this orientation, the inlet 41 of the channel 40 is located above the blade 20, thereby increasing the likelihood of aspirating smoke rising from the blade 20.

The channel inlet 41 can be angled downwardly toward the blade 20 to further increase the effectiveness of the suction. The angle of the channel inlet plane relative to the axis of the blade 20 can range from 30 to 90 degrees, but is preferably approximately 45 degrees when angled.

Also, to increase the effectiveness of the smoke suction, it is desirable to position the inlet 41 as close as possible to the incising tip of the cutting portion 21. However, the placement of the channel inlet 41 over the end of the blade 20 can interfere with the user's view of the incision site. To maximize the proximity of the channel inlet 41 relative to the end of the blade 20 while reducing obstruction of the surgeon's view of the blade tip, the top wall 12 can taper downwardly at the front end 14 of the handle 10. The channel inlet 41 can thereby be positioned close to the blade end, perhaps within 3 mm, without significantly interfering with the surgeon's view.

In the preferred configuration of the channel inlet 41 above the blade 20, the inlet portion of the channel 40 is disposed above the blade 20. As the channel 40 extends rearwardly to the outlet 42, the channel 40 transitions from an upper extension adjacent the top wall 12 to a lower extension parallel to the bottom surface 16 of the handle 10. To effect this transition, the channel 40 preferably curves laterally to avoid engagement with the mounting shaft 25 of the blade 20 and then curves back to a parallel alignment with the inlet end of the channel 40 near the rear of the handle 10.

Referring to FIGS. 2, 3a and 3b, the curved region 43 of the tube 44 curves both downwardly and laterally to accomplish the transition from the upper to the lower extension. As shown in FIG. 3a, the curved region 43 extends laterally to avoid intersection with the blade mounting shaft 25 as the curved region 43 extends downwardly as shown in FIG. 2. As the channel 40 extends rearwardly past the blade contact 33, which generally represents the rearward termination of the mounting shaft 25, the curved region 43 curves back to a central, parallel alignment with the inlet portion of the channel 40. The resulting electrosurgical device provides an integral smoke aspirating means which provides an inlet 41 above the incising blade 20 while minimizing the thickness of the associated handle for housing the aspirating means. Thus, an optimally placed inlet for aspirating smoke is combined with a slender electrosurgical device handle.

FIG. 3b, which is an axial sectional view along line 3b—3b in FIG. 1, illustrates the vertical location of the rearward portion of the channel 40 below the separating wall 18 and the wire 30 in the upper cavity. As shown in FIG. 3a, the channel 40 extends rearwardly to the channel outlet 42 which can be formed in an integral adapter end 42 constructed to slidingly mate with a standard hospital suction tube for evacuation of smoke drawn through the channel 42.

Figure 4:
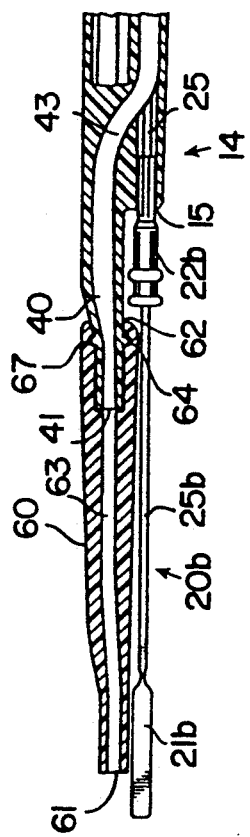
FIG. 4 is a side sectional view of a breakaway forward end of the first embodiment, showing use of an extended blade and suction extension.
Figure 5:
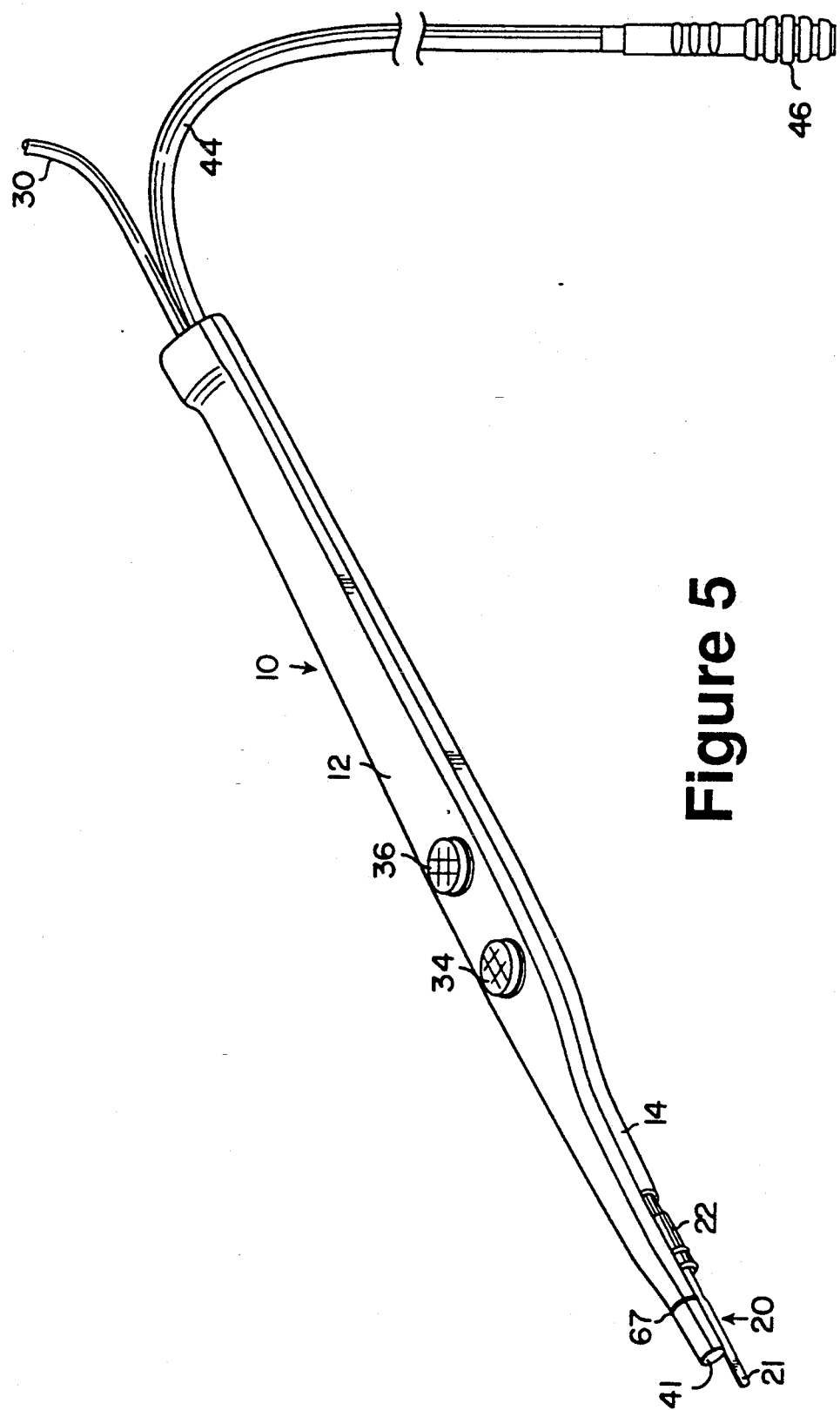
FIG. 5 is a perspective view of a second embodiment of an electrosurgical device, wherein the smoke aspirating means additionally includes an aspirating tube partially disposed in the handle.
Figure 6:
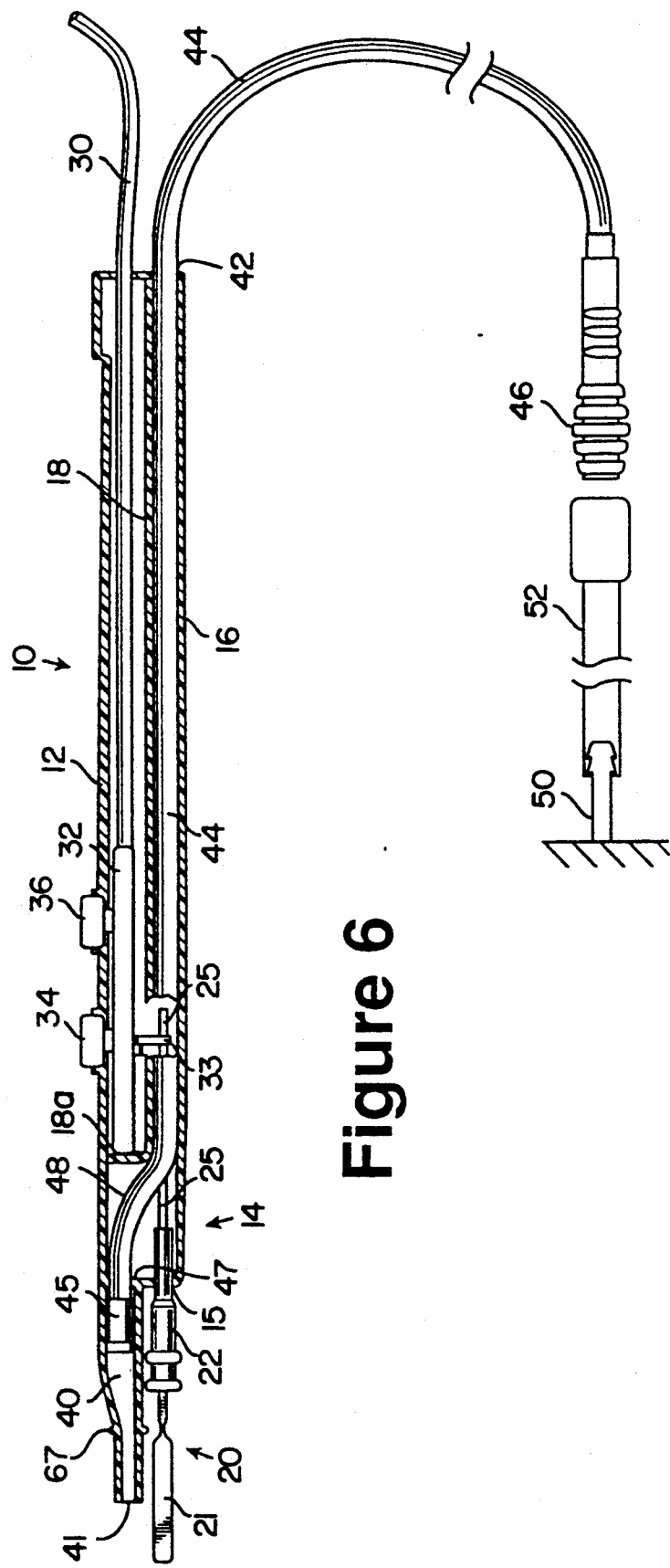
FIG. 6 is a side sectional view of the second embodiment.
Figure 7:
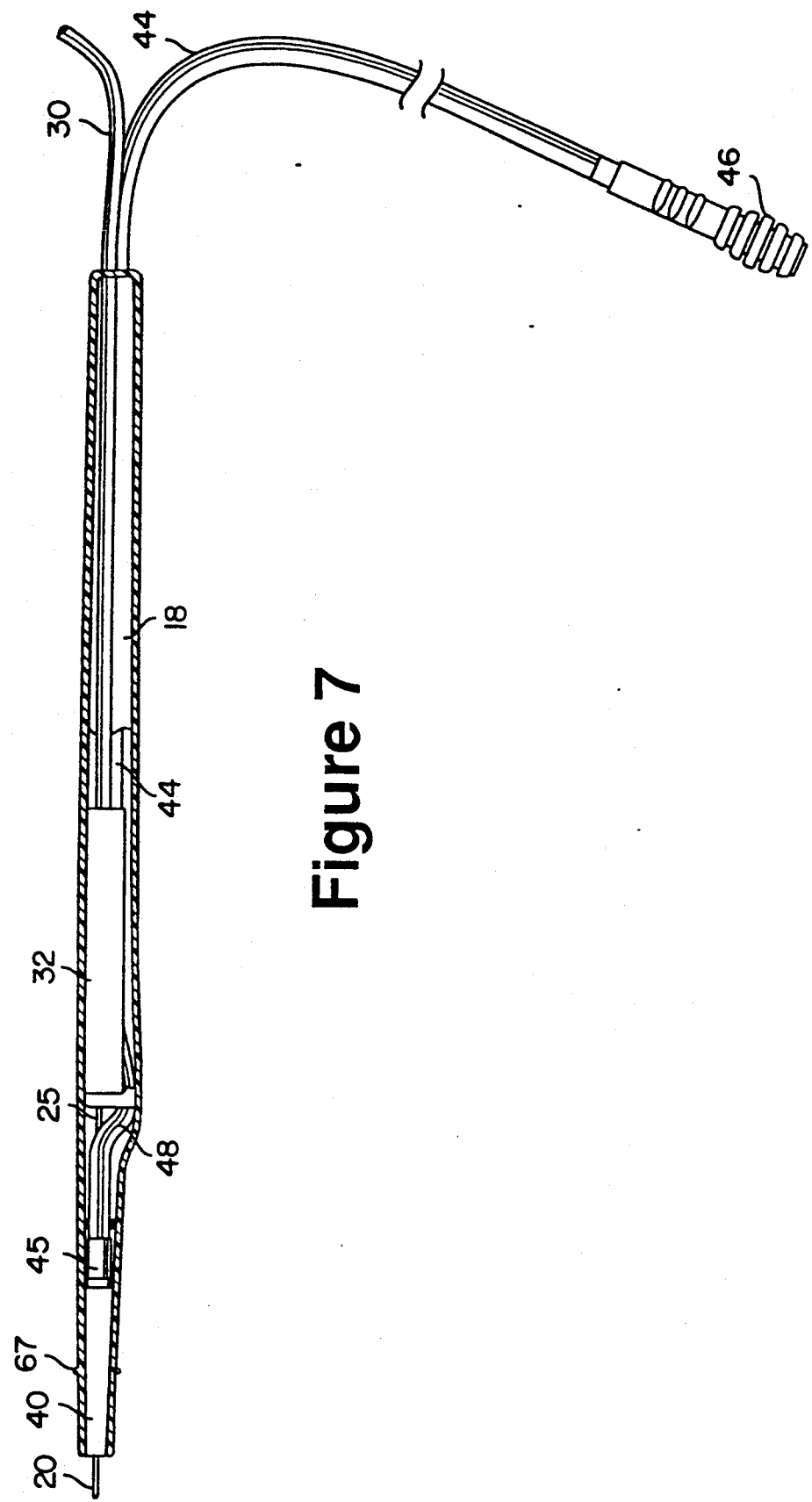
FIG. 7 is top sectional view of the second embodiment.
Figure 8:
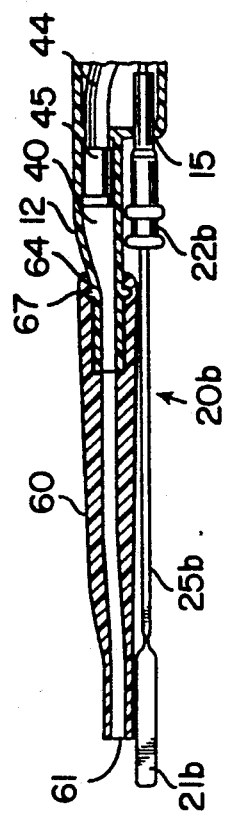
FIG. 8 is a side sectional view of a breakaway forward end of the second embodiment.
Figure 9:
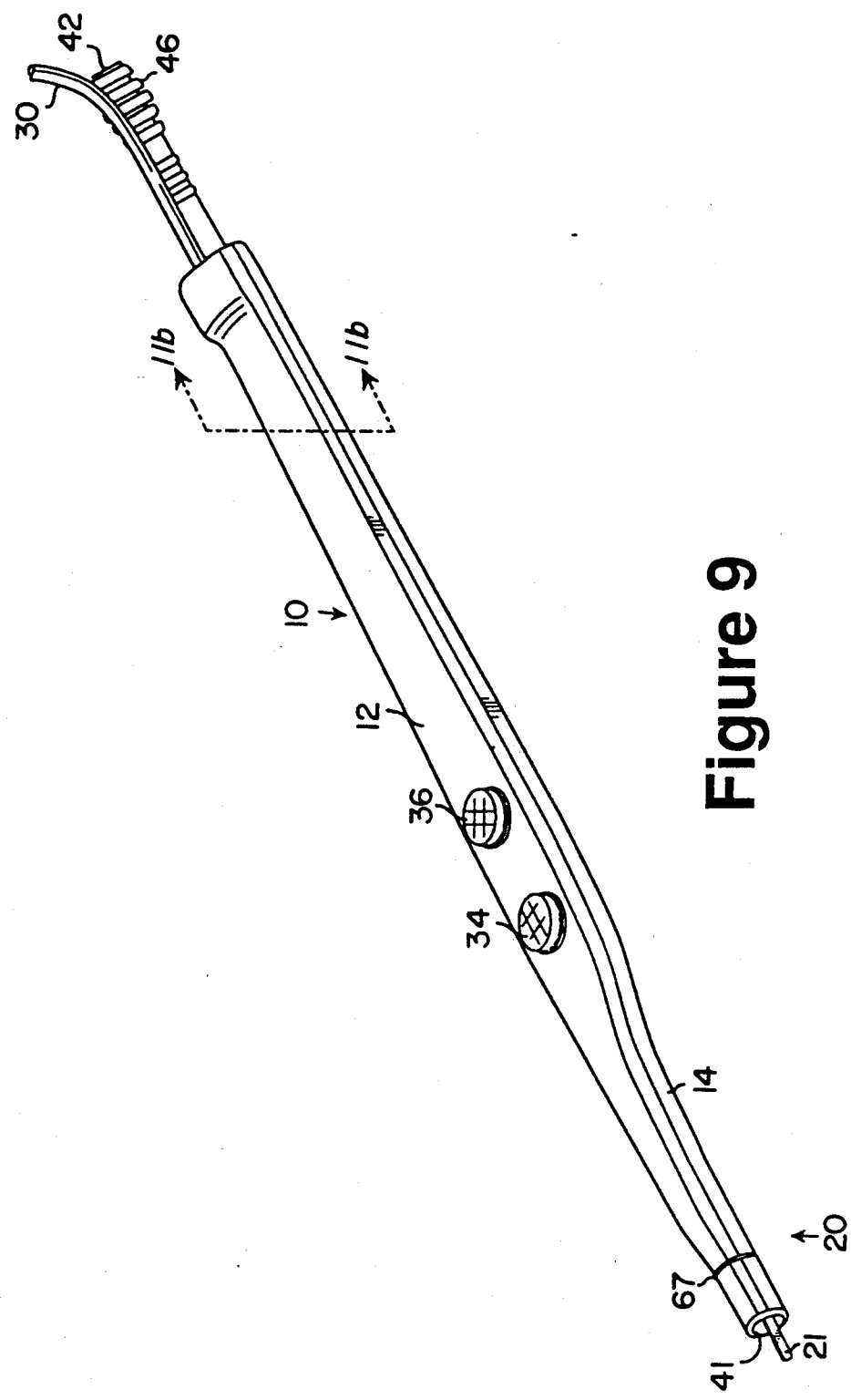
FIG. 9 is a perspective view of a third embodiment of an electrosurgical device, wherein the channel inlet of the handle surrounds the electrosurgical blade.
Figure 10:
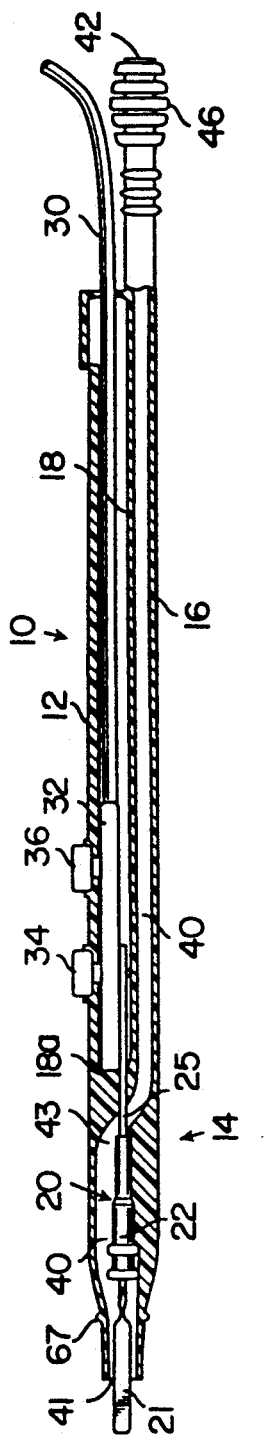
FIG. 10 is a side sectional view of the third embodiment.
Figure 12:
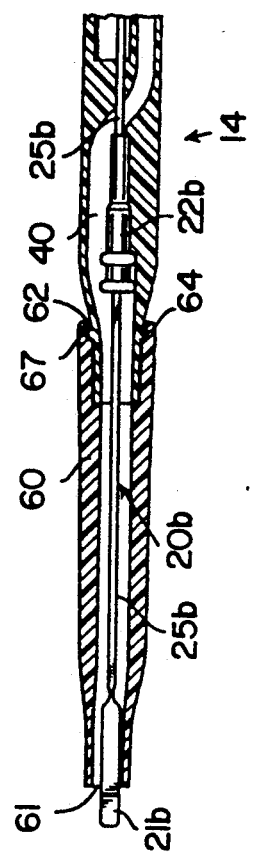
FIG. 12 is a side sectional view of a breakaway forward end of the third embodiment.
Figure 13:
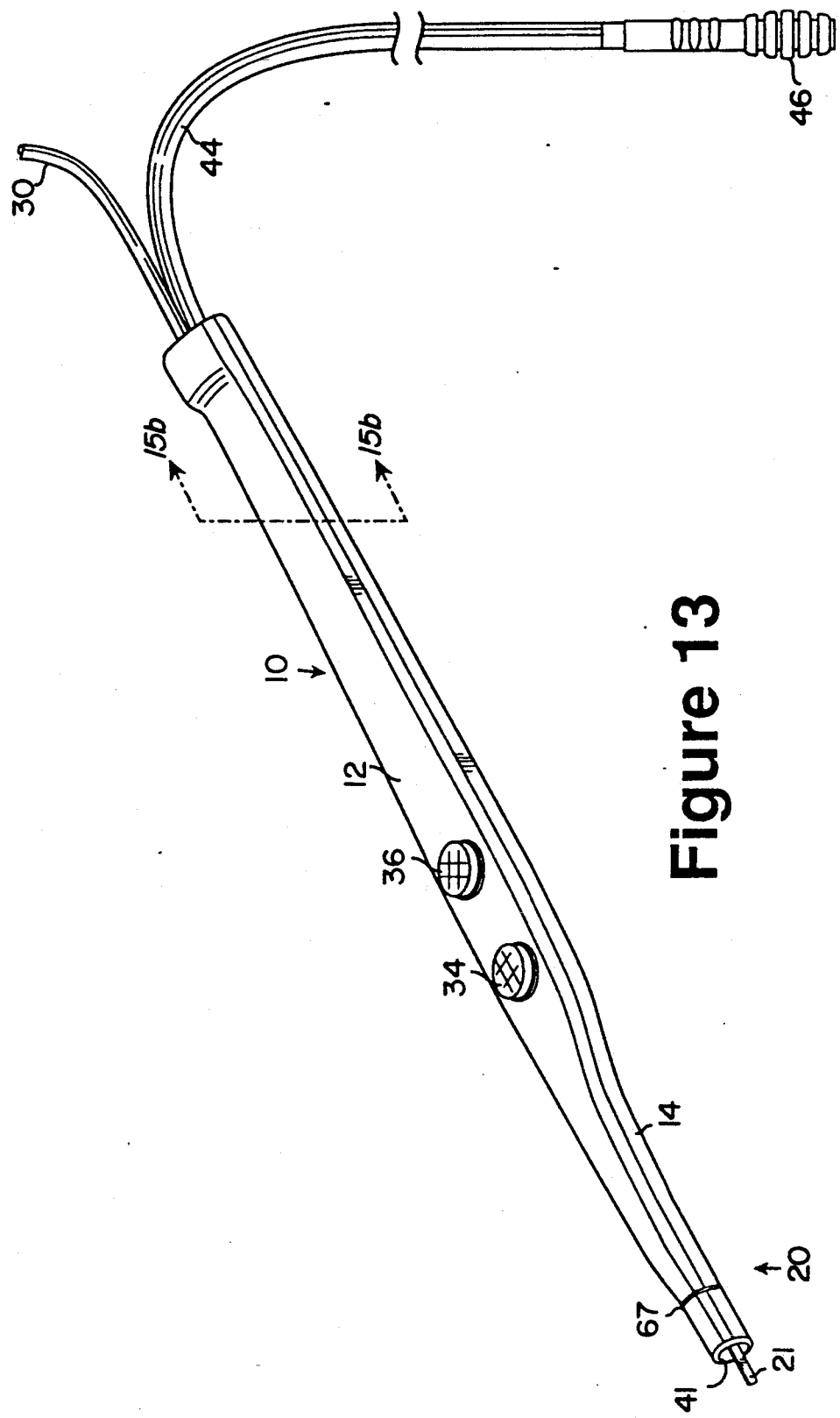
FIG. 13 is a perspective view of a fourth embodiment of an electrosurgical device, wherein the channel inlet surrounds the electrosurgical blade and evacuates smoke through a suction tube connected to the interior channel.

Referring to FIG. 4, the electrosurgical device can also be equipped with a suction extension 60 to draw smoke produced by incision with an extended blade 20b. The extended blade 20b, which can be used in closed space procedures, includes a cutting member 21b disposed at the end of an elongated shaft 25b, which can be several inches in length. The extended blade 20b can be interchanged with other blades and provides a mounting sleeve 22b for manual removal and insertion of the blade 20b through the mounting aperture 15.

The suction extension 60 provides a channel 63 which is readily aligned with the channel 40 of the handle 10. The diameter of the extension channel 63 can be enlarged at the outlet end 62 to surround the inlet end of the handle 10, thereby maintaining a constant diameter along the length of the extension 60 and channel inlet 41.

The suction extension 60 is preferably constructed as a rigid, plastic tube having an intake 61 formed adjacent the cutting member 21b. The opposite, outlet end 62 can be formed to slidingly mount onto the inlet end of the channel 40. The outlet end 62 can also provide an annular groove 64 for lockingly engaging a detent ring 67 formed on the outer wall of the handle 10. The suction extension 60 is securely held by the detent ring 67 and extends substantially parallel to the extended blade 20b. Because of the thermoplastic rigidity, the preferred suction extension 60 is securely positioned without lateral support. The suction extension 60 is therefore not susceptible to the random position changes which can occur with a flexible catheter suction tube.

Referring to FIGS. 5-8, a second embodiment of the invention is shown in which like numerals to those in FIGS. 1-4 are used to reference like components and structure.

Although the channel 40 is sufficient alone for communicating smoke through the handle 10, the aspirating means can also include an aspirating tube 44 extending through the channel 40 and away from handle 10 for connection to a conventional hospital suction tube 52 or directly to a suction source such as a vacuum port 50, generally known in the art. The tube 44 is preferably a no. 14 French catheter, but can be constructed of other materials and sizes. The external end of the tube 44 is preferably equipped with conventional suction tube adapter 46 for attachment to the conventional hospital suction tube 52.

The tube 44 can be secured in the channel 40 in a variety of ways. The tube 44 can be pressure fit against the walls of the channel 40 during construction of the handle 10. Alternatively, the tube 44 can be adhered to the walls of the channel 40 by suitable adhesives. The tube 44 can be secured in the channel 40 and prevented from withdrawal by an end sleeve 45 connected to the inlet end of the tube 44. The sleeve 45 can be positioned proximate the inlet 41 of the channel 40 and secured against retraction towards the outlet 42 by a retaining flange 47 formed in the walls of the channel 40.

In an alternative assembly, the inlet end of lightweight tube 44 can be secured in the handle 10 proximate the channel 42 outlet rather than extending through the channel 40 to the channel inlet 41. This construction can facilitate manufacturing while maintaining the advantages of using a catheter as a lightweight conduit for smoke traveling from the handle 10 to the relatively bulkier hospital suction tube 52. In either construction, the device provides lightweight maneuverability with reliable smoke aspiration.

Referring to FIGS. 9-12, a third embodiment of the invention is shown in which like numerals to those in FIGS. 1-8 are used to reference like components and structure. The third embodiment of the electrosurgical device provides an inlet 41 of the integral channel 40 which encircles the blade 20. The blade 20 extends into the channel 40 and through the forward wall 18a to electrically connect to the control circuitry 32.

During use, the shrouding inlet 41 draws smoke produced by incision or cauterization with the cutting member 21 independent of the orientation of the handle 10. If the handle 10 is curved sideways for a particular incision, the shrouding inlet 41 provides an upper passage to effectively capture smoke rising from the point of incision. In other respects, the third embodiment of the electrosurgical device as shown in FIGS. 9-12 is similar to the first embodiment shown in FIGS. 1-4.

Referring to FIGS. 13-16, a fourth embodiment of the electrosurgical device is shown in which like numerals as those used in FIGS. 1-4 represent like components and structure. The fourth embodiment of the invention combines the features of the shrouding inlet 41 with the features provided by the use of the suction tube 44 connected to the handle 10 within the channel 40.

Figure 14:
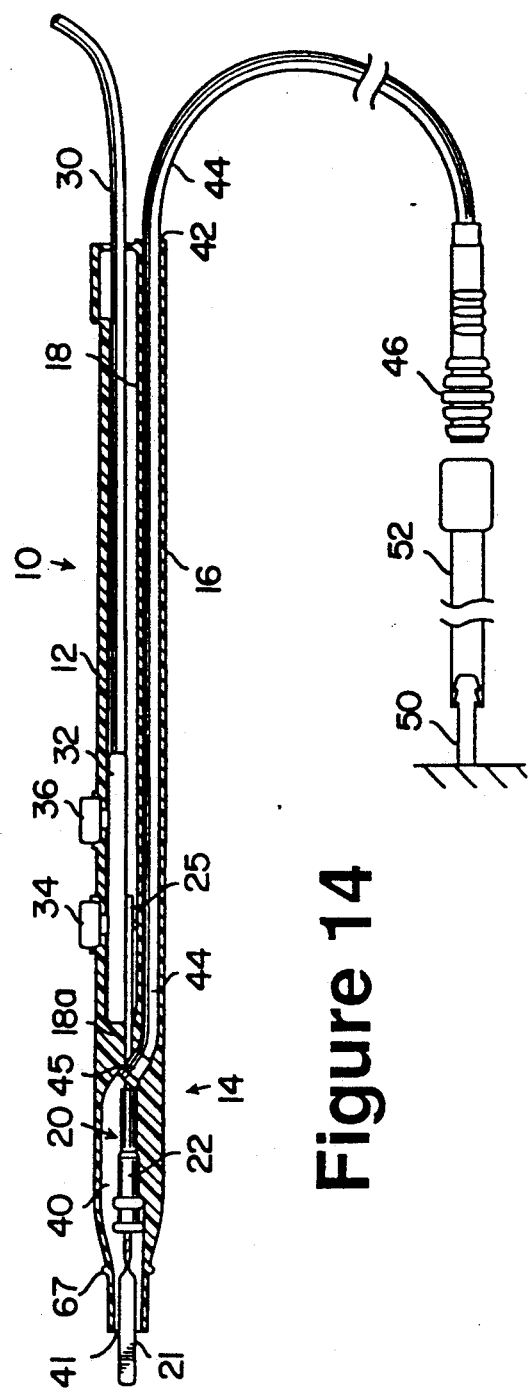
FIG. 14 is a side sectional view of the fourth embodiment.
Figures 15A, 15B:
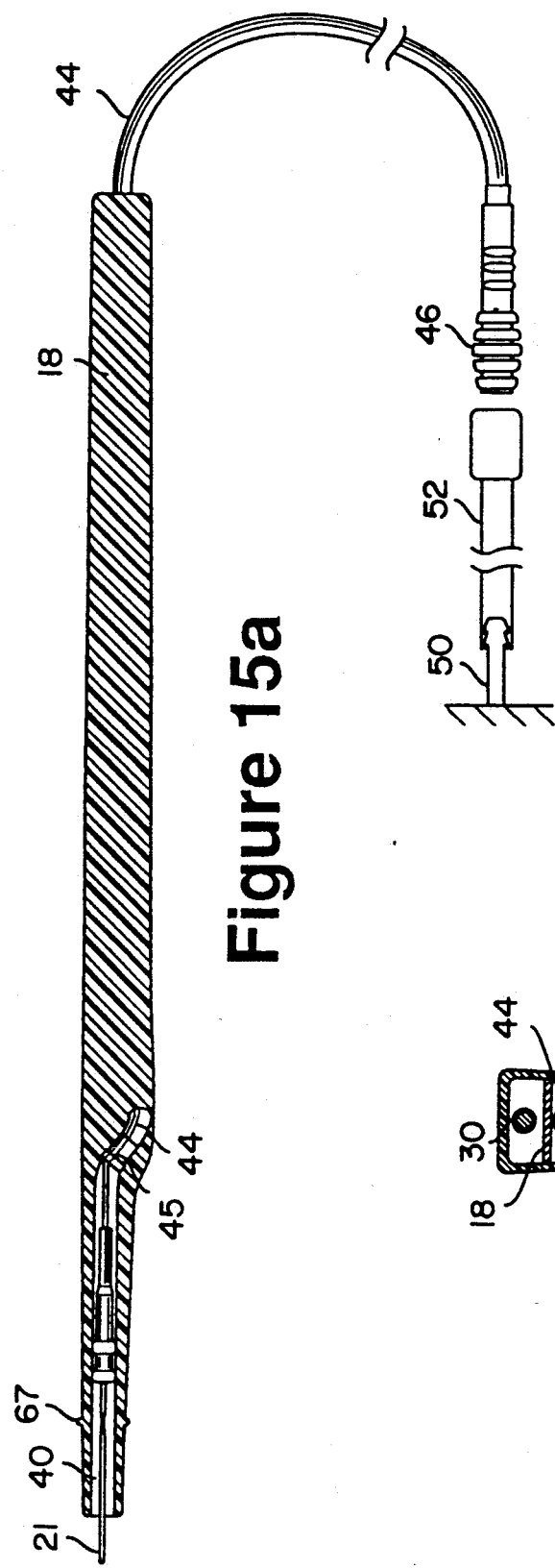
FIG. 15a is a top sectional view of the fourth embodiment.
FIG. 15b is an axial sectional view along line 15b—15b in FIG. 13.
Figure 16:
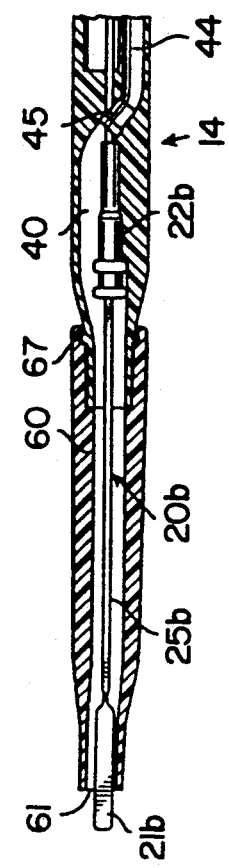
FIG. 16 is a side sectional of a breakaway forward end of the fourth embodiment.

Referring to FIG. 14, the inlet end of the tube 44 with sleeve 45 is disposed in the channel 40 in a median position remote from the inlet 41. This median location can facilitate manufacture while maintaining the advantages of the use of a lightweight tube 44 in connection with the channel 40. Alternatively, the inlet end of the tube 44 can be disposed adjacent the channel outlet 42.

Thus, the invention provides a disposable, easily manufactured, lightweight electrosurgical device which effectively evacuates smoke produced by electrosurgical incision. The integral channel can readily be adapted for superficial or closed space smoke aspiration without the disadvantages attendant to prior devices.

While preferred embodiments of the invention have been described in detail, it will now be apparent to those skilled in the art that various modifications and alternatives to those details can be developed in view of the overall teachings of this disclosure. For example, the aspirating means can alternatively be provided by a channel formed in the side of the handle. The side channel can extend axially from an inlet on the left or right of the blade to a rear outlet. The aspirating means can also provide a channel inlet above the blade and a channel which extends rearwardly along an interior of a side of the handle without transitioning to a lower extension along the bottom wall of the handle. Accordingly, the particular arrangements disclosed are meant to be illustrative only and not limiting as to the scope of the invention, which is to be determined by a reasonable interpretation of the appended claims.

I claim:

1. An electrosurgical device for incising anatomical structures and evacuating smoke produced thereby, said device comprising:
   an electrically conductive blade for incising said anatomical structures;
   an elongated handle for holding and manipulating said blade, said handle having a first axial end to which said blade is connected;
   an electric connecting means for electrically connecting said blade to an electric power source;
   electric control means positioned along a top of the handle for switching electric power to said blade; and
   aspirating means for permitting passage of said smoke through said handle, wherein said aspirating means includes an interior channel formed by said handle, said channel extending from a channel inlet at said first axial end to a channel outlet at a second axial end of said handle opposite said first end and wherein said channel inlet is separated from and disposed above said blade along a top side of said blade, said inlet thereby capturing smoke rising from said blade.

2. The electrosurgical device according to claim 1, wherein said aspirating means further includes a tube disposed in said channel and extending out from said channel outlet for connection to a vacuum source.

3. The electrosurgical device according to claim 1, wherein said channel inlet is disposed less than 5 mm from a front end of said blade.

4. The electrosurgical device according to claim 1, wherein said handle is made of thermoplastic material, whereby said aspirating means is rigidly positioned relative to said blade.

5. The electrosurgical device according to claim 1, further comprising a suction extension removably mounted to said handle at said channel inlet and extending axially from said first axial end, said suction extension having an intake for passage of smoke from and extended end of said blade through said suction extension to said channel inlet where said smoke is further evacuated through said handle.

6. The electrosurgical device according to claim 5, wherein said suction extension is constructed of a rigid material whereby said suction extension can extend from said handle without lateral support.

* * * * *